United States Patent [19]

Reutter et al.

[11] Patent Number: 5,625,037
[45] Date of Patent: Apr. 29, 1997

[54] ANTIBODIES, METHOD OF PREPARING SAME, OLIGOSACCHARIDES AND CLONES FOR PROVIDING SAID ANTIBODIES, AND THE USE OF SAID ANTIBODIES FOR TUMOR DIAGNOSIS AND THERAPY

[76] Inventors: Werner Reutter, Arnimallee 22; Rolf Nuck, Sodenerstrasse 34, both of 1000 Berlin 33; Martin Zimmermann, Dominicusstrasse 44, 1000 Berlin 62, all of Germany

[21] Appl. No.: 128,264

[22] Filed: Sep. 28, 1993

Related U.S. Application Data

[63] Continuation of Ser. No. 556,960, filed as PCT/DE89/00146m Mar. 8, 1989, abandoned.

[30] Foreign Application Priority Data

Mar. 8, 1988 [DE] Germany .......................... 38 07 594.6

[51] Int. Cl.$^6$ ..................................................... C07K 16/30
[52] U.S. Cl. ................... 530/387.5; 530/388.85; 530/389.7; 436/813
[58] Field of Search .................... 530/387.5, 388.85, 530/389.7; 436/813; 435/70.21, 172.2, 240.27

[56] References Cited

PUBLICATIONS

Becker et al., Cell Surface Glycoproteins of Hepatocytes and Hepatoma Cells Identified by Monoclonal Antibodies. Biol. Chem. Hoppe–Seyler 367:681–688, 1986.
Becker et al., Biol. Abstr. 82(11):100773. 1986.
Riese et al., Biol. Abstr. 84(12):120471. 1987.
Chemical Abstracts 86: 104294r (1977).
Chemical Abstracts 105: 189019p (1986).
"Diagnose und Labor", 36, 41–54 (1986).
"Biochemistry 1985", 24, 4665–4671.
"The EMBO Journal", 5(9), 2109–2114 (1986).

*Primary Examiner*—Mary E. Mosher
*Assistant Examiner*—Donna C. Wortman
*Attorney, Agent, or Firm*—Wenderoth, Lind & Ponack

[57] ABSTRACT

Antibodies against N-glycan structures of cell membrane surfaces and showing in an ELISA test a positive reaction against antigenic oligosaccharides, said antibodies comprising chitobiose-mannose-trisaccharides.

3 Claims, No Drawings

ANTIBODIES, METHOD OF PREPARING SAME, OLIGOSACCHARIDES AND CLONES FOR PROVIDING SAID ANTIBODIES, AND THE USE OF SAID ANTIBODIES FOR TUMOR DIAGNOSIS AND THERAPY

This application is a Continuation of now abandoned application Ser. No. 07/556,960, filed Jan. 8, 1990, which is a continuation of PCT/DE89/00146, filed Mar. 8, 1989.

The invention relates to novel antibodies directed against the oligosaccharide portion of glycoproteins, methods of preparing said antibodies and oligosaccharide-haptens and clones for generating these antibodies. The novel antibodies are suited for tumor diagnosis and therapy as they are capable of signalling the organ-specific structural units of tumor-relevant glycoproteins and can intervene in the glycoprotein chemistry of the cell membrane surfaces of malignant tumor tissue by bonding with said glycoprotein.

In the past, antibodies were generated by immunization against whole cells, membrane fragments or isolated membrane glycoproteins or lipids; in the latter case the complete molecule of the protein serves as antigenic determinant. In contrast, no attempts have been made so far to generate antibodies—and to test them in sera—separated from the protein portion of the glycoproteins. Since in the glycoproteins, the protein portion dominates the carbohydrate portions as an antigenic determinant, the antibodies recovered so far were directed predominantly against the protein structure. In this way, the formation of appreciable amounts of antibodies against cell-typical oligosaccharide structures of glycoproteins was prevented. For this reason, it has not been possible in the past to trace and show the presence of microstructural features and deviations in the glycan portion.

For some time, it has been common practice in tumor diagnosis to measure certain serum glycoproteins, primarily fetal proteins and carcinoembryonic antigens, see G. Uhlenbruck and F. Dati (1986). For the laboratory diagnosis of tumor conditions, see Diagnose & Labor 36, 41–55. If a relatively advanced tumor is present, increasing amounts thereof may be shown to exist in serum, but they are relatively unspecific. A higher specificity is obtained by measuring human choriongonadotropin (hCG), which is positive in some relatively rare gonadal and uterine tumors, see Henry S. Kaplan, L. Olsson and A. Ranbitschek (1982), "Monoclonal Human Antibodies: a recent development with wide-ranging clinical potential", Monoclonal Antibodies in Clinical Medicins (ed. by A. McMichael and J. W. Fabre), Academic Press. London, N.Y., p. 16–35).

The usefulness of measuring the activity of fucosyltransferase for tumor diagnosis in serum has been tested as well, see C. H. Bauer. W. G. Reutter, K. P. Erhart, E. Kötgen and W. Gerok (1978), "Decrease of Human Serum Fucosyltransferase as an Indicator of Successful Tumor Therapy", Science 201, 1232–1233. They are quite as meaningful as conventional tumor markers. They also have produced positive values in thyroidal carcinoma; this has not been possible with the aforesaid markers. Still, it has not been possible using these enzymes to obtain substantial improvements in tumor diagnosis. Presumably, the problem of organ-specific diagnosis calls for a solution which differs substantially from the methods employed so far. In the recent past, the use of monoclonal antibodies has been found to be very useful in lymphoma diagnosis and characterization, see H. Stein and D. Y. Mason (1985), "Immunological analysis of tissue sections in diagnosis of lymphoma", Recent Advances in Haematology, A. V. Hoffbrand et al. (ed.), Livingstone.

One of the objects underlying the invention is to provide specific antibodies which enable glycoproteins and glycoprotein patterns to be detected more specifically than in the past so as to diagnose and treat cells and cell modifications such as occur in tumors and metastases.

Glycoproteins constitute essential components of plasma membranes because they a) make up 60% of the plasma membrane (e.g. in the liver), b) provide the contact between the cell and its environment as well as neighboring cells, and c) recognize externally arriving information and transfer it into the cell.

Malignant transformation changes the glycoprotein pattern of the plasma membrane, see P. Vischer and W. Reutter (1978), "Specific Alterations of Fucoprotein Biosynthesis in the Plasma Membrane of Morris Hepatome 7777", Eur. J. Biochem. 84, 363–368; T. Galeotti, A. Cittadini, G. Neri, S. Papa and L. A. Smets (1985), "Cell Membranes and Cancer", Elsevier, Amsterdam. These alterations are accompanied by a disturbed transmission of information, unregulated growth and finally the release of some cells from tissue metastazation.

The following have been found as alterations of the glycoprotein compositions:

a) The disappearance of liver-specific glycoproteins, b) The appearance of novel glycoproteins c) Changes of the carbohydrate portion of protein-similar glycoproteins.

As a result, an alteration of the glycoprotein pattern the normal cell is known to have allows a conclusion to be drawn as to the presence of malignant degeneration.

At this time, the diagnosis of tumors in general and of hepatocarcinoma in particular is unsatisfactory. The subject matter of the invention is the detection of certain tumor-specific membrane proteins or membrane protein patterns in the serum of tumor patients, particularly of patients afflicted with hepatoma.

In accordance with the invention, it has been found that the carbohydrate portion in cell membrane glycoproteins, when separated from the protein composite, constitutes an extraordinarily specific antigenic determinant for the provision of antibodies. For this reason, the inventive antibodies are specific against N-glycan structures of cell membrane surfaces. In the ELISA test, they react positively against antigenic oligosaccharides with structural elements of chitobiose mannosetrisaccharides. According to their chemical structure, the inventive antibodies constitute class G and H immunoglobulins having a molecular weight in the range of 100,000 to 900,000. Their effect is optimum in the 20° to 40° C. temperature range.

The inventive antibodies are prepared by separating the oligosaccharide fraction from of cell membrane surface glycoproteins, coupling the haptens and then using them immunologically as antigens for producing antibodies. The oligosaccharide fraction is separated chemically (e.g. by hydrazinolysis) or enzymatically by using suitable enzymes such as amidase F (E.C. 3.2.2.18), endoglycosidase F (E.C. 3.2.1.96) and H (E.C. 3.2.1.96). (The numbers are equal since separation takes place in the same position.)

Initially, the oligosaccharide fraction is purified and then separated into the various oligosaccharide bodies, if needed. The isolated oligosaccharides are coupled chemically in the form of haptens to a suitable vehicle such as albumin or edestin and then used as antigen for forming antibodies.

The generation of antibodies may be polyclonal or monoclonal in nature.

Suitable carriers for hapten coupling are, in particular, albumin and edestin.

If polyclonal, the preparation of the antibodies is performed preferably by injecting a micellar antigen suspension into the dorsal skin of a test animal and recovering the antibodies from the blood serum fraction. Suitable test animals are, in particular, rabbits or chicken.

If monoclonal, the preparation of the antibodies is performed preferably by injecting a test animal with the antigen-coupled hapten; various strains of mice such as Balb/c, NSI, NSO or of rats such as Y3 and YB2/0 are particularly useful. Following the recovery of the spleen cells of the immunized animal, they are fused with myeloma or plasmacytoma cells of Balb/c mice (such as X.63/Ag8653) and the antibodies recovered from the medium of the recloned positive clones.

These clones form a subject matter of the invention as well.

The structural variety and the degree of ramification of the oligosaccharides in the glycoproteins is much greater than that of the linear proteins. For this reason, it was surprising that the antibodies are obtainable in a highly differentiated and even monospecific form, whereby a group of immunological structural sensors has been created which are cabable not only of differentially recognizing the structure of normal glycoproteins; they also can diagnose the glycoproteins with a modified carbohydrate fraction of the kind formed by tumor cells.

In the course of the invention, it has been possible to analyze and identify the glycoproteins of normal and malignant cell membranes. All N-glycan-oligosaccharides are based on a chitobiose mannosetrisaccharide substituted in different amounts and positions by L-fucose, D-mannose, N-acetyl-D-glucosamine, lactosylamine and N-acetylneuramine acid. The number of the monosaccharide units is from about 6 to 24. A characteristic feature is the high fucose and mannose proportion that can be found in the case of mature tumor cells.

The interaction of structural antigenicity and antibody activity is much more differentiable in the field of oligosaccharides having structures according to formula I and thus more sensitive than on proteins. This opens an avenue to organ-specific tumor diagnosis.

The inventive antibodies offer the possibility of reaching the peripheral regions of a cell, which communicate with the surrounding environment and the neighboring cells; they do not have to penetrate down to the protein fraction, which is anchored much more deeply in the cell surface (lipid double layer).

The novel diagnostic procedure offers the following advantages:

It results in the generation of antibodies against surface structures which are more accessible than the protein carriers embedded in the membrane;

The cell or organ specificity is based primarily on oligosaccharide structure and composition.

The antibodies are identified by an ELISA test (enzyme linked immunoabsorbent assay). To this end, the antigen (cell or membrane extract) is applied to a plastic surface (e.g. into the wells of 96-well-microtitration plates), allowed to dry (30 min.), then incubated with IgG of mice (=the antibodies to be tested), washed three times with buffer solution (PBS=phosphate buffered saline), then incubated with antimouse IgC's of sheep coupled with an enzyme such as peroxidase (2 hrs. at room temperature), washed with PBS. After the addition of the substrate orthophenylidenediamine (200 µl) and stopping the reaction by 5 µl of 0.1M NaF (the reaction is monitored about 2 hrs.), the color developed—which is proportional to the amount of antibodies—is read through a spectrophotometer.

The membranes of tumor cells have a glycoprotein complement other than that of corresponding normal cells. Glycoproteins of the plasma membranes are shed to the serum by a) the secretion of such glycoproteins as may preliminarily form components of plasmamembranes, b) by shedding and c) by cell aging and decay.

It is unlikely that all kinds of hepatocarcinoma express a common specific glycoprotein which may be used as a tumor marker. For this reason, individual monoclonal antibodies were used in accordance with the invention to characterize a glycoprotein pattern corresponding to a normal liver membrane. This pattern was selected so that it will be altered by malignant transformation. Specifically, isolated membrane glycoproteins of the liver (eight) and of hepatoma (eight) were tested. The detection of an altered glycoprotein pattern in the patient serum signalled a malignant transformation or a nascent hepatocarcinoma.

In the production of antibodies against membrane glycoproteins, antibodies have never been produced separately against the protein fraction and the carbohydrate fraction and tested in tumor patient sara. In accordance with the invention, antibodies have now been prepared for the first time against both the oligosaccharide fraction and the protein portion and tested in tumor sera. The inclusion of the carbohydrate fraction of membrane glycoproteins as an antigenic determinant greatly broadens molecular tumor diagnosis.

In particular, eight membrane glycoproteins of each of the liver and of Morris hepatomas have been isolated successfully. Monospecific antibodies were prepared against these glycoproteins. It has been shown with the aid of immunoprecipitation that at least two of the glycoproteins (DPPIV, gp80) are present both in the liver and in hepatoma. Gp80 is released into the serum by normal liver cells, with its glycan structure in the serum differing from that of the membrane protein. It has not been ascertained so far whether and which amounts of gp80 are released into the serum by a hepatoma.

It has been possible also to ascertain the presence of other membrane glycoproteins in the serum or in supernatant culture liquor of primary hepatocytes. It has been possible further to prepare monospecific antibodies which recognize only a single glycoprotein of the hepato membrane (Mr 175 k). This glycoprotein is fucosylated to a particularly high extent.

Further, a series of monoclonal antibodies has been provided which are directed against glycoproteins of the plasma membrane of normal hepatocytes.

| Monocl. Antibody | Antigen | Remarks |
| --- | --- | --- |
| 9.1 | 110, 135 kD | |
| 9.2 | 110 kD | Does not occur on hepatoma. Localized at the gall-canalicular membrane of the hepacytes and additionally in the small intestine and in the salivary glands. |
| 11.1 | 170 kD | Does not occur in hepatoma. |
| 11.3 | 130 kD | Occurs in high concentrations in liver and hepatoma cells. |

| Monocl. Antibody | Antigen | Remarks |
|---|---|---|
| 15.2 | 70 kD | Directed against alkaline phosphatase, occurs also in hepatoma. |

Additional antibodies were prepared; as far as the antigens are characterized, all of the oligosaccharides obtained are covered by general formula II.

It has been found that in hepatoma and renal tumors the oligosaccharide structures of membrane glycoproteins in hepatoma and renal tumors differ characteristically from those of normal tissue.

Poly- and monoclonal antibodies have been prepared against such tumor-specific oligosaccharides as well. To this end, tumor membranes were isolated, the oligosaccharide fraction separated (enzymatically and chemically, where necessary) and antibodies induced against that fraction. Because of the likelihood of a cross reactivity between humans and rats and for ease of access, the initial testing (including testing for usefulness as markers) was conducted on oligosaccharides from plasma membranes of hepatomas chemically induced in rats. It may be assumed that the investigations may be applied to human material.

In addition to hepatoma oligosaccharides, corresponding investigations were conducted with oligosaccharides from other tumors, particularly tumors of the colon.

The Preparation of Antibodies

Isolation of subcellular membrane structures from tumor or metestatic tissue by homogenization of the tissue in a buffer A, consisting of 10 mM $NaHCO_3$ and 0.5 mH $CaCl_2$, pH 7.0, and subsequent multiple centrifugation. First centrifugation: 20 minutes at 1500 g, sediment pickup in buffer A and subsequent homogenization in an Ultraturrax or a Dounce homogenizer. Second centrifugation: as above. In this way, the sediment is washed a total of four times. Thereafter, the oligosaccharide structures are recovered from the sediment. This is effected either chemically by hydrazinolysis or enzymatically by means of amidase F. Chemical decomposition: hydrazinolysis of the dried (lyophilized) sediments (10 hrs. at 100° C.) by adding 0.5 to 5 ml of freshly distilled anhydrous hydrazine to 100 mg to 1 g of membrane fraction and 8 to 12 hrs. holding at 100° C. (according to S. Takasaki, T. Mizouchi and A. Kobata in Methods in Enzymology (1982), vol. 83, 263–277); thereafter, the reaction mixture is heated (1 hr.) and concentrated in vacuum (over concentrated $H_2SO_4$ at ambient temperature) for drying. The residue is treated by repeated evaporation with toluene and then dissolved in saturated $NaHCO_3$. Enzymatic separation of the oligosaccharide side chains by means of amidase F (E.C. 3.2.2.18): To 10 to 100 mg of lyophilized membrane fraction is added a 1% sodium dodecylsulphate solution (=SDS) in water and mercaptopropanol or merceptoethanol (end concentration 100 mH) and treated, ultrasonically, held at 100° C. for 1 minute, then received in 0.5M phosphate buffer, pH 8.6, with 1% Mega-10 (=octanoyl-N-methylglucamide) added thereto, and treated ultrasonically again. Amidase F (12 mU per milligram of protein, separates 1 nmol oligosaccharide per minute) is added to separate the oligosaccharides (24 hrs. at 41° C.). Separation of the oligosaccharides is effected in a column filled with BioGelP4, smaller than 400 mesh (1.6 cm×300 cm) and gel permeation chromatography, as well as by anion exchange high-pressure liquid chromatography in a column filled with Partisil AX-10, 2×4.6×250 mm and a descending gradient of $H_2O$/0.15M $KH_2PO_4$, pH 4. Gel permeation chromatography allows separation to be effected according to the number n of monosaccharides in an oligosaccharide fraction (n=1–22), whereas anion HPLC allows oligosaccharide fractions to be separated in accordance with charge differences due to N-acylneuraminic acids (=sialic acids) or sulphate. For the preparation of antigens from these haptens, the oligosaccharides are coupled to bovine serum albumin or edestin (method of Kunz and Waldmann, Angewandte Chemie (1985) 24, 883–885) as follows: The oligosaccharide is peracetylated by means of acetic anhyride/pyridine, suspended in a fresh cold-saturated hydrogen chloride solution in acetyl chloride and stirred for 24 hrs. at ambient temperature. After the solvent has been distilled off, the residue is recrystallized from acetone/ether. The oligosaccharide so obtained is dissolved in anhydrous formamide while adding sodium azide (20 mols azide per mol of oligosaccharide) and stirred for 2 hrs. at 80° C. The reaction mixture is poured onto 100 ml $H_2O$ and the aqueous phase extracted three time with $CHCl_3$. The united organic phases are dried over $MgSO_4$, concentrated and the residue recrystallized from acetic ester/ether. From this oligosaccharide azide, the oligosaccharide amine is obtained by dissolving the azide in ethanol and adding platinum oxide hydrate (100 mg per mol of azide). After 2 hrs. at ambient temperature, the deposit is filtered off and the filtrate concentrated. For preparing the completely protected oligosaccharide/asparagine/albumin compound (peracetylated oligosaccaride-$N^2$-(tert.-butyloxycarbonyl) -L-asparaginallyl-ester), the oligosaccharide amine is dissolved with Boc-Asp-OAII (mol/mol) in methylene chloride and ethyl-2-ethoxy-1,2-dihydroquinoline-1-carboxylate (EEQD) added in an 1.5 molar excess. After 3 days of stirring at ambient temperature, the allyl ester crystalline out. Impurities are separated chromatographically with acetic ester/petroleum ether (1:1) and the product eluted with acetic ester. Decomposition of the allyl ester is effected in anhydrous and oxygen-free tetrahydrofuran and dimethylsulphoxide by adding tetrakis(triphenylphosphine) palladium(o) under argon and the exclusion of light. Thereafter, a 10× molar excess of morpholine is dripped in. After 4 hrs., the solvent is distilled off in a high vacuum and the product purified chromatographically.

Mono- and polyclonal antibodies are prepared against those oligosaccharide fractions which may be shown quantitatively to exist in tumors. The monoclonal antibodies are prepared according to the process of Köhler and Milstein (Nature (1975) vol. 256, 495–497): Balb/c mice are injected with 10 to 20 µg antigen three to four times in 10 day intervals. Four days after the last (booster) injection, the spleens are removed from the mice, the spleen cell recovered and fused with myeloma cells (NS-1) under addition of polyethyleneglycol (end concentration 38%). The positive cell clones are recloned and the monoclonal antibodies recovered from the medium. The antibodies are purified by Affi-Gel-Blue chromatography followed by HPLC chromatography (TSK-3000 SW column) according to Josic, Schütt, van Renswoude and Reutter (J. Chromatogr. (1986) Vol. 353, 13–18); according to more recent procedures, a protein A-eupergit column (Eupergit C30N by Röhm Pharma; eupergit is an activated polyacrylamide).

The polyclonal antibodies are produced by mixing the purified antigen with oil to form a micellar suspension and intracutaneous injection (10–20 spots) in the dorsal skin of a rabbit. The first injection contained Freundsch adjuvant, the following 2 to 4 injections did not. The injections were administered in 3 to 4 week intervals. The blood (from the ear artery or vein or from the heart) is centrifuged and the antibodies are recovered from the serum fraction in the manner described above.

We claim:

1. Isolated and purified antibodies capable of specifically binding to a glycan moiety of a tumor cell membrane surface glycoprotein and Immunoreacting positively against antigenic oligosaccharides containing said glycan moiety, said glycan moiety having the formula:

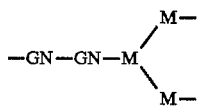

where GN represents N-acetylglucosamine, M represents —D— mannose, and wherein the mannose groups are joined to each other through a 1,3- or 1,6-glycosidic bond.

2. Antibodies as claimed in claim 1 prepared monoclonally by:

a. separating and isolating oligosaccharide fractions of glycoproteins from tumor cell membrane surfaces;

b. coupling the oligosaccharide fractions, as haptens, to a carrier to form an antigen;

c. injecting the antigen into a test animal having a spleen, to immunize said animal against said antigen;

d. recovering the spleen cells of the immunized animal, which spleen cells produce antibodies including the desired ones;

e. fusing the spleen cells with myeloma or plasmocytoma cells;

f. culturing said fused cells;

g. selecting from said fused cells those which produce antibodies which react specifically with said glycan moiety as the desired antibodies;

h. culturing said selected fused cells; and i. recovering the desired antibodies from said cultured and said selected fused cells.

3. Antibodies as claimed in claim 1 wherein said carrier is bovine serum albumin or edestin.

* * * * *